United States Patent [19]
Boratyn

[11] Patent Number: 6,136,329
[45] Date of Patent: Oct. 24, 2000

[54] COMPOSITIONS AND METHODS RELATING TO INTRA-LAMELLAR GELS FROM ALGAE

[76] Inventor: Diane C. Boratyn, 3135 W. Government Way, Seattle, Wash. 98199

[21] Appl. No.: 09/089,849

[22] Filed: Jun. 3, 1998

Related U.S. Application Data

[60] Provisional application No. 60/048,659, Jun. 4, 1997.

[51] Int. Cl.[7] ..................................................... A61K 7/00
[52] U.S. Cl. ..................... 424/401; 424/70.1; 424/70.13; 424/70.14; 47/1.4; 514/54; 514/57
[58] Field of Search ................................ 424/70.1, 70.13, 424/70.14, 401; 514/54, 57; 47/1.4

[56] References Cited

U.S. PATENT DOCUMENTS

| | | | |
|---|---|---|---|
| 3,917,816 | 11/1975 | Yueh | 424/61 |
| 3,939,260 | 2/1976 | Lafon | 424/28 |
| 5,653,970 | 8/1997 | Vermeer | 424/70.24 |
| 5,741,482 | 4/1998 | Modi | 424/76.3 |

FOREIGN PATENT DOCUMENTS 1296793  11/1972  United Kingdom.

OTHER PUBLICATIONS

Shaughnessy et al. Reliability of the resorcinol method for identifying isomorphic phases in the Gigartinaceae Rhodophyta.J. Appl Phycol. 1991. vol. 3(2), 121–128.

Shaughnessy et al. Reliability of resorcinol method for identifying isomorphic phases in the Gigartinaceae (Rhodophyta). vol. 3, pp. 121–127, 1991.

*Primary Examiner*—Thurman K. Page
*Assistant Examiner*—Lakshmi Channavajjala
*Attorney, Agent, or Firm*—Graybeal Jackson Haley LLP

[57] ABSTRACT

Although compositions from seaweed have long been sought after for beneficial properties for the skin, the ability to produce efficacious compositions has been elusive. An intra-lamellar gel, produced from marine algae, has been found to enhance the condition of skin and hair. Milt, optionally in combination with intra-lamellar gel, also provides a composition useful for application to the skin or hair.

8 Claims, No Drawings

COMPOSITIONS AND METHODS RELATING TO INTRA-LAMELLAR GELS FROM ALGAE

CROSS-REFERENCE TO RELATED APPLICATIONS

This application claims priority from U.S. provisional patent application No. 60/048,659, filed Jun. 4, 1997, which is incorporated by reference.

TECHNICAL FIELD OF THE INVENTION

The present invention relates to compositions and methods relating to extracts from algae and/or fish milt as ingredients in skin and hair care products.

BACKGROUND OF THE INVENTION

Seaweed has historically been sought after for beneficial properties for the skin. Maintaining these properties in a suspended state is a difficult matter. Additionally, the smell and feel of the seaweed have generally been a deterrent to wider market acceptance. Recovery of beneficial properties in an economical way has been difficult. Further, efficient recovery of beneficial properties generally involves the use of materials that may be considered undesirable for skin and hair care. Current treatments leave room for improvement with regard to producing long term benefits in a variety of skin and hair types.

In addition, many combinations of treatments for the hair and skin, both chemically and naturally formulated, are in use today. Of the treatments for hair one known factor that affects the quality of the end user product is protein, which is believed to bond to the hair shaft. Such protein may be derived from various sources (e.g., silk protein) and may have varying levels of efficacy depending on the source, extraction or processing methodology, interactive quality and quantity used alone or with other products. Fish milt is a high content protein source and also comprises essential fatty acids. Proteins are also important to the skin supporting collagen production. Methods and compositions for collagen use and production in the skin have long been sought in cosmetic and skin and hair care communities.

Accordingly, there has gone unmet a need for compositions and methods from seaweed that provide superior beneficial properties for the skin and hair, and for sources of protein that likewise provide superior benefits for the skin and hair. The present invention provides these and other related advantages.

SUMMARY OF THE INVENTION

The present invention provides compositions and methods that are useful for application to the skin or hair. The compositions and methods provide a youthful and healthful look to the skin and fullness to the hair, among other benefits. The compositions comprise a milt and/or an extract from algae, referred to herein as "intra-lamellar gel," optionally in combination with an oil. The intra-lamellar gel is useful for skin care because it provides a protective covering, and it also leaves skin smooth and soft while the skin is exfoliating. The intra-lamellar gel provides apparent face "lifting" via wrinkle smoothing properties both in short and long term results. The processing methodology enhances the beneficial properties of the compounded materials to deliver the highest quality of nutrients while lifting the skin. When the intra-lamellar gel is produced with an essential oil, the gel may also provide aromatherapeutic effects. A complex diversity of benefits to the skin and hair can be added to the above through the use of a variety of essential oils. For example, the intra-lamellar gel can function as a carrier across the skin. Selection of desired essential oils can enhance this function.

These and other aspects of the present invention will become evident upon reference to the discussion herein. In addition, various references are set forth herein that describe in more detail certain procedures or apparatus. All such references are incorporated herein by reference in their entirety.

DETAILED DESCRIPTION OF THE INVENTION

As used herein, the term "intra-lamellar gel" refers to a composition comprising intracellular algae materials produced with water, fresh algae and oil, using the methods described below. The gel can be extracted from between the lamella of an alga. For example, the intra-lamellar gel can be obtained from between the interior space that is created between the two lamella, or walls, that make up a blade of many types of algae. "Blades" are the broad, membranous distal portions of kelp plants or other foliaceous algae. The intra-lamellar gel may include galactans, (a phycolcolloid substance), phycobilins, inner cellular matter, auxiliary cells, valves and support cells and may be comprised of $\alpha$ and $\beta$-carotenes, amino acids, bromine, calcium, chlorine, iodide, iron, chlorophyll, phycoerythrin, manganese salts, mucins, protein and/or sodium. The intra-lamellar gel may also include portions of exterior wall substances or by-products from processing. Preferably, the intra-lamellar gel is fluorescent An oil, such as an essential oil, may be added to intra-lamellar gel. As described herein, the intra-lamellar gel is preferably made using at least one essential oil, and therefore the gel includes some fraction of the distilled oil(s) that has been integrated into the substance through processing. The properties of the intra-lamellar gel can be tailored due to selection of appropriate oils for the gel, which selection is within the ordinary skill of the art in view of the present specification.

Turning to algae generally, there are over ten thousand members of the algae family, and they can have structures that vary from single celled entities to plants that extend over several hundred feet in the ocean and grow to become the largest plants on earth. It may be that algae in the ocean manufacture more hydrocarbons through photosynthesis than all land plants combined. Because algae live in the water they do not need supporting structures like cellulose and lignin. Instead, algae contain substances inside and outside their individual cells that support the life processes in the water. Such substances are mixtures of many substances, including complex polysaccharides, that can have strong gel-like properties. For example, the substances can form large molecules comprising chains of atoms (potentially more than 200,000) that can form a stiff gel at a concentration of only 1 percent. Such substances are used to make dental impressions, stabilize ice cream, and form emulsions. They are also used as suspending agents in soft drinks and as emollients and thickeners in cosmetic creams and locations. They are typically colorless and tasteless, impart a slippery feeling, and form a thin protective film on the surface of the skin or hair.

Preferred varieties of algae suitable for use in the present invention include Mazzaella (also known as Iridaea) and Condracanthus (also known as Gigartina). Mazzaella typically grows in a thin strata in the mid to northern end of the Puget Sound, Wash., U.S.A., preferably where there is an outcropping of hard clay. The algae are both membranous or foliar, and potentially have carrageenan content. Carrageenan is a phycolloid characteristic of some Rhodophyceae (such as Gigartinaceae), and is a sulfated galactan located extracellularly; various fractions are recognized based on solubility differences. Suitable species of Condracanthus include *exasperatus*.

Another preferred species is *Fucus gardeneria* (preferably the Bladderwrack variety). The intra-lamellar gel is taken primarily from the receptacle portion of the plant. Because of the nature of the plant, it has a slightly stinging quality when applied to the facial skin, perhaps because the extract component includes alginic acid. The intra-lamellar gel is a clear, thick pale yellow-green substance.

A further preferred species is Nori, preferably using Lemon Oil as the essential oil in the extraction process. Considerable amounts (approximately 4 oz. from 2 blades) of intra-lamellar gel were extracted. It is relatively clear with a purple hue. However, the intra-lamellar gel so produced does not appear to have as long a shelf life as with intra-lamellar gels extracted from Mazzaella and Condracanthus. Other suitable species include *Chondrus crispus* (Irish Moss), and a green kelp obtained from Puget Sound. Small amounts of intra-lamellar gel were produced using the same methodology as with the other species discussed herein.

Still another preferred species is *Rhodophyta* (red algae), which algae may comprise chlorophyll a (d in some Florideophyceae), R- and C-phycocyanin, allophycocyanin, R-and B-phycoerythrin, a and B-carotene and several xanthophylls, thylkoids (single, not associated). A significant storage product is floridean starch (amylopectin-like). The cell walls may comprise cellulose, xylans, several sulfated polysaccharides (galactans), calcification, and alginate. In some of the species of red algae, there can be an auxiliary cell that is helpful to fertilization, such as with *gigartinales* where the support cell or normal intercalary cell of the mother plant is set aside as an auxiliary cell before fertilization. The tetrasporangia are cruciate or zonate.

Other suitable species of algae will be apparent to a person of ordinary skill in the art in view of the present specification (see, for example, Bold and Wynne, *Introduction to the Algae* (Prentiss Hall 1978), and references cited therein). In general, all large algae are suitable for use in accordance with the present invention. For example, the following algae are suitable as sources of intra-lamellar gel: *Fucus Gardeneria, Fucus Gardeneria vesiculosis, rhodophyceae, gigartinales, gracilariaceae, phyllophoraceae,* Gigartinaceae, *Gigartina exasperata, Gigartina stackhouse, Gigartina california, Iridaea splendens, Iridaea bory, rhodoglossum, chondrus* and *chondrus crispus*.

The intra-lamellar gel compositions described herein are preferably produced with at least one oil. Optionally, the gel can be supplemented with additional oil after production. Suitable oils include synthetic oils, such as neroli, and essential oils, such as eucalyptus. As an illustration, suitable oils include angelica, lemon balm, melissa, bergamot, cedar, chamomile, clary, cypress, eucalyptus, hyssop, immortelle, jasmine, lavender, lemon, lemongrass, lemon verbena, mint, spearmint, peppermint, myrtle, neroli, orange, rockrose, rose, rosemary, sandalwood, swiss pine, betiver, yarrow, ylang-ylang, basil, bay, cajeput, camphor, carrot seed, cinnamon, clove, geranium, grapefruit, line, majoram, niaouli, patchouli, pettitgrain, rosewood, sage, tangerine, tea tree, thyme, vanilla, and self-heal. Preferred oils include clary, eucalyptus, lavender, lemon, neroli, rosemary, cajeput, grapefruit, sage, and thyme.

Turning to some preferred essential oils suitable for use with the present invention, eucalyptus oil (*Eucalyptus globulus*) can be distilled (steam) and include eucalyptol (typically about 80–85%) as a primary component and may include butylaldehyde, fenchen, globulol, isoamylalcohol, camphen, capronaldehyde, pinen, pinocarveol, terpineol, sequiterpene, sesquiterpenal alcohol, valeraldehyde. Eucalyptus oil can be germicidal, and can increase oxygen by activating red blood cell function. It can have antiseptic effects for the skin or other target tissue, may act as a regenerative deodorant. The oil may also have estrogen producing qualities and aid with skin blemishes and acne. It also can act as a dandruff reducer on hair. Essential oils with some properties in common can include niaouli, pine, Swiss pine, hyssop and thyme.

Lemon oil (*citrus limomum*) can be extracted by cold pressing and may include camphen, pinen, aldehyde, phellandren, methylhepton, a-terpinen, limonen, citronol, terpineol citral, linalyl-, neryl-, citronellyl-, geranyl-acetate, cadinen, acetic acid, caprin acid, lavrin acid, citroten, vitamin C. Lemon oil can act as an astringent, antibacterial, antiseptic, cleanser, and may promote cell regeneration (anti-aging). Lemon oil can also reduce sebum production in oily skin and tighten skin. It may be slightly bleaching in highly concentrated form and can be used to treat freckles. Lemon oil may also help with brittle fingernails and toenails, chapped and rough skin and healing wounds. On the hair it makes it shine, including blond hair, and it may help with dandruff and oily hair. Essential oils with some properties in common can include lavender, Swiss pine, ocean pine, cedar, eucalyptus, fennel, juniper.

Lavender oil (*lavendula officinalis*) can include linalylacetat (30% to 60%), linalylbutyrat, linalylvalerianat, lunalylcapronat, furfurol, amyl-alcohol, B-ocimen, ethyl-n-amylketon, D-α-pinen, cineol, D-borneol and acetate, L-linalool, geraniol, nerol, caryophyllen, cumarin, lavendulol, and different fat aldehydes. Lavender oil can provide deodorizing, balancing, regenerative, circulatory stimulant, detoxifying, and tonic qualities to a user. It may be antibacterial, antifungal, antiseptic, anodyne and is valued as a medicinal oil. It can help with the treatment of acne, burns and fluid retention. It may also be used in treatment of athlete's foot and as an insect repellent. Good for all skin types, particularly dry skin. When applied to hair it may affect hair loss and dandruff. Essential oils with some properties in common can include bergamot, orange, lemon, geranium, clary, pine, Swiss pine, neroli and rose.

Thyme oil (*thymus vulgaris*) can be distilled and it main constituents can include thymol, caracrol, and terpene. Thyme oil can act as an antiseptic, may help to form white blood cells and can be used in natural cosmetics. It may increase circulation, promote metabolism and help with oily and damaged skin. It can invigorate the scalp, and be suitable for hair treatments, possibly including preventative hair loss treatments.

Neroli oil (*Citrus aurantium*) can be distilled and may include B-ocimen, L-α-pinen, L-camphen, dipenten, L-linalool, L-linalylacetate, phenylalcohol, α-terpinal, nerol, nerylacetate, geranium, nerolidol, farnesol, acetic acid, indol, benzoe acid, anthranil acid, methylester, and parafine. Neroli oil can be beneficial for all skin types and can help with sensitive, dry and inflamed skin, aging skin and broken veins. It may also have regenerative and deodorant properties. Essential oils with some properties in common can include rose, lavender, sandalwood, jasmine, cedar, geranium, lemon.

Algae should be harvested from marine sources. It is possible to harvest algae blades exceeding 3–4 feet in length (although blades of almost any length can be used), which typically come from greater depths than the tidal zones. Such species have been known to grow 40 to 60 feet deep.

Alternatively, algae can be grown in tanks in a controlled aquaculture environment. In such a situation, the timing of harvest can be controlled by the user.

Algae may be processed up to 50 hours, or even 2–3 days, after harvesting if the algae is kept moist. Preferably, however, algae is processed within 4–5 hours after harvesting.

Harvested algae can be processed as follows. First, blades or other suitable algae parts are rinsed. Non-suitable blades are discarded or utilized for fertilizer. Preferably, an essential oil is first placed in water in a container and then allowed to disperse. Heavy gauge stainless steel is a preferred container for a brewing to produce the intra-lamellar gel. Selected blades are placed in the water, preferably with an essential oil, for a "brewing cycle" from about 4–8 hours to about 8–48 hours, preferably from about 8 to 22 hours. Typically, 3 to 5 pounds of algae were combined with 5 to 10 quarts of water, and 1 to 5, preferably, 2.5 to 3, tablespoons of oil.

Preferably, at least two cycles of heating and cooling are used during brewing, during which a minimal amount of alternating low heat is applied. Also preferably, the temperature of the water is raised to about 115° F. to 135° F., but preferably not above about 125° F.–49° C. If the temperature is too hot, it may harm the intra-lamellar gel. Once the desired temperature is attained, the heat source is turned off and the material is allowed to settle into a brew cycle for a period of about 2–10 hours, preferably about 5–8 hours at temperatures that hover between about 70° F. low and about 105° F. high. After this cooling period, the cycle can repeated one (or more) time(s) until the intra-lamellar gel is ready for the next phase; cycling can continue as long as desired, but over-heating, which can easily be determined empirically, can deteriorate the ultimate product.

Preferably, the intra-lamellar gel should be extracted from the algae shortly after the brewing is completed in order to avoid deterioration such as off-odor, bacterial contamination, and cloudiness of the gel and the rinseate. First, the blades are removed from the brewing water (or rinseate or rinse water) and placed in a colander or on paper towels, or gently hung at a sloped angle to help coagulate the gel. The water is drained off. The blades containing the newly formed intra-lamellar gel can remain in this suspended state from up to 24 hours, or from about 3 to 15 hours, and preferably, to about 8 hours. Next, the blades are held to the light and then individually "milked" (preferably hand expressed) into glass containers and then strained once or twice for clarifying purposes. The resulting isolated intra-lamellar is placed in desired containers, preferably air tight. A preferred example is a special packet using inert gas techniques to seal the intra-lamellar gel. It should be noted that the rinseate, although dilute, can also be used as a source of intra-lamellar gel.

Intra-lamellar gel can be used on skin such as facial skin and/or the hair. For example, the intra-lamellar gel can be applied smoothly with thick strokes to the face and neck for about 20 minutes for a face lift and line smoothing or rubbed in for a finished look with lifting qualities. It produces similar results in men and women. A teaspoon to tablespoon applied to the hair and scalp, after washing and conditioning, produces a finishing result with great body that has been well absorbed into the hair strands. Intra-lamellar gel acts as a high absorption and protectant in hair, possible estrogen producing qualities, tightening and lifting of skin, exfoliation, clarifying possibly through acid found within, and texture and absorption providing a "finished" more youthful look to skin.

Intra-lanellar gel is also active in the medicinal arena. For example, it was used as a skin protector and to speed healing as in the areas of burns and wounds. Intra-lamellar gel was applied directly on a second degree burn on an inner arm. It faded the scar in about 6 months, which normally may take up to 2 years to fade well. The intra-lamellar gel was also used as a mosquito repellent in a jungle near Nairobi, Kenya for 10 nights, and the user did not suffer any mosquito bites where the intra-lamellar gel had been applied. The intra-lamellar gel can also be used as a skin protectant to protect against external agents, and it can reduce outbreaks and enhance clearing of acne/skin eruptions/blemishes. Moreover, intra-lamellar gel can be used in formulations to lighten skin color. Preferably, skin-lightening compositions also contain eucalyptus oil.

Intra-lamellar gel can also serve as a base substance for other useful agents. For example, intra-lamellar gel can be used with substances used in cosmetics, such as collagen, placenta, and elastin. Moreover, intra-lamellar gel can be used as a base substance in liquid homeopathic preparations that include substances such as St. John's Wort and ginko.

As noted above, there are additional beneficial effects when the intra-lamellar gel comprises one or more essential oils.

The following discusses some of the preferred uses in more detail. The intra-lamellar gel can be used full strength or diluted or in combination with other desirable substances, include fish milt, as discussed further below.

Intra-lamellar gel may be used as a hair gel to provide body, sheen and hold to hair with little or no "gumming" qualities. The gel sinks into hair with no residue feel, and it can be used on wet and dry hair. The gel appears to produce a cationic and anionic response on the hair strand. It has been found that about 1 tablespoon or more can be well absorbed into fine hair. The gel can be applied after shampoo and/or conditioner.

Intra-lamellar gel can also be used as a face and neck mask to tighten and lift skin (like a face lift but with no surgical techniques), eliminating lines and wrinkles while mask is on face. For this purpose, the gel has been found to have some effect even on a person of 83 years. Preferably, the gel is left on a minimum of about 20 to 30 minutes. The subject can be either horizontal or vertical, although vertical is not recommended for those with severely sagging skin, until they have used the intra-lamellar gel for at least about ½ year. In some instances, repeated layers of gel may be applied to attain enhanced results, as the skin usually absorbs substantial amounts of the intra-lamellar gel in the first few applications and may need to be thick before a protectant layer is formed.

Each area around the face, eyes, and neck represents different skin types; the neck being the more sensitive than the face. The intra-lamellar gel has been used successfully under the chin to and neck to tighten and firm. Around the eyes it relieves sticky or itchy, droopy morning eye feeling by cooling and opening the eye. Eyes have a brighter, more awake appearance after using the intra-lamellar gel. Intra-lamellar gel may be used to the lash line. It leaves the skin soft and smoothed with tightened pores and can lighten skin having darker tones.

Overnight administration of the intra-lamellar gel may produce long term results of fine line elimination and/or reduction along with tightening and toning of skin, particularly in the area around the eye.

The intra-lamellar gel can also be used as a body gel and skin finisher. It can tighten skin and reduce cellulite appearance.

Some preferred uses when the gel is at an about 25%–99% concentration, by weight or volume depending upon the desires of the user, include as a face gel and cream, an eye gel, a body gel and skin "finisher" or as a hair treatment. It can also be used for or with cosmetics, preferably at concentrations between about 1%–25%.

Intra-lamellar gel has additional uses. For example, the gel can be used to mark animals, such as fish, due the fluorescent properties of the gel.

The term "milt" is used herein in its usual sense to refer to the fluid from fish testes that comprises sperm. As used herein, however, the term also applies to such fluids from other animals, unless the context clearly indicates otherwise.

The milt, preferably fish milt, is applied to hair or skin to enhance the thickness, strength and other beneficial characteristics of such hair and skin. In one preferred embodiment, the milt is used in combination with soap based products (particularly shampoo), and water that enhances the effect of the milt proteins with the hair and skin. A further enhanced desired effect is achieved when fish milt is used in combination with the algae intra-lamellar gel from algae discussed herein. Preferably, a composition comprising milt does not contain added alcohol.

On the hair, the invention improves current methods of shampooing and conditioning by adding a step wherein the milt is added to the shampoo, which has already been applied to the hair, and thus changes the appearance and feel of the shampoo. Such methods create increased shine, better texture, body and manageability for hair. The milt-shampoo treatment is reported to reduce "frizzies." Further, the product provides healthy restoration of damaged hair. When treated hair is examined under the microscope, the milt appears to smooth the hair shaft in damaged locations. Typically, one milliliter of milt is used per application.

Results from a variety of test users have been positive, even if the hair type varies. In fine limp and treated hair the hair becomes more full bodied, thicker and shinier. Curly and frizzy hair relaxes to a more manageable, shinier state while retaining body. Color treated and damaged hair regains at least a portion of a healthy feel to the touch. Gray hair, which is usually coarse and difficult to manage, becomes soft and shiny with body.

Severely damaged hair is preferably treated at least about 5 times with the milt. After such multiple treatments, the hair appears to require no further heavy applications. Continued use of milt can provide long lasting, possibly semi-permanent, restructuring results. Intra-lamellar gel may be used to maintain healthy feel and shine along with protecting the hair shaft.

On the skin, in simple application (one time usage), milt can be used instead of, or in combination with, well known methods of chemical and gylcolic acid peels and thereby providing exfoliation and increased circulation and absorption without major abrasive irritation due to the milt. Preferably the milt is used under the supervision of a skin care specialist.

In some preferred embodiments, the milt is obtained from salmon (for example, chinook, chum, silver, king or pink) or cod. Cod milt, is thicker and heavier than salmon milt, and is preferably extracted by compression to separate the milt from the milt sac of the fish. Such milt may have particulates from sac, but these do not disturb the efficacy of the product when applied to the hair and skin. In some instances where the hair or skin is very dry, it may be preferred to use this format.

The milt is preferably extracted from a live fish. The milt may be in a pre-motility state when removed from the fish. The isolated milt, typically 4–5 ml, can placed in any suitable container, such as a small plastic bags, and is preferably flooded with oxygen and sealed. The milt can vary from an iridescent white to slightly salmon pink if tinged with blood during the removal. The milt is preferably stored under refrigeration, for example about 40° F., or the temperatures found in a standard refrigerator. Optionally, the milt may be stored frozen. The typical maximum shelf life well prepared milt is about 12 days, although longer periods are acceptable if greater amounts of the milt are used for the application to the hair or skin.

The milt deteriorates after a certain time period. The milt can be frozen if desired in order to retard such deterioration, and is still effective for at least some purposes even if thawed by microwaving. Preferably, for example to meet a year around high end demand market, the milt can be frozen in a nitrogen chamber at peak harvesting times of the year, worldwide, at similar aquaculture sites, then thawed and packaged in atmosphere altered containers. Deterioration can also be inhibited by combining antibacterial agents such as the essential oil thyme with the milt, and/or packaging in an oxygen-free environment.

The following discusses some preferred methods of applying milt to the hair and skin, although the milt can be used in any sequence or combination with other hair/ skin care products.

Hair is moistened with water and then shampooed with any commercially available shampoo or soap for 1–2 minutes. About ½ to 1 ml of milt is added to the hair while the shampoo is still in the hair. The milt is then worked thoroughly into the scalp and hair. In preferred embodiments, the shampoo then de-lathers, removing what is considered sudsy properties of soap, and becomes silky flat. The milt and shampoo are then left on the hair for any desired length of time, typically about 3–5 minutes, then rinsed. In some preferred embodiment, upon addition of the rinse water, the combined milt and shampoo swell volume, up to about 10 times, into a luxurious mousse, silken state in the hair. This is then rinsed out with additional water, preferably until the rinsing water is clear.

The milt can also be mixed with a hair conditioner in any desired concentration, typically from about 2 ml milt to about 10 ml conditioner to about 10 ml milt to about 2 ml conditioner. The combined conditioner and milt causes the conditioner to attain a silken, flat state but it does not typically expand in the manner that shampoo can.

Turning to skin, milt can be used as a facial wash or wash for other skin. The milt can also be combined with lotions, emollients and/or soap. Preferably, the combination of milt and soap provides a product that, in turn, forms a light, silky, creamy texture in use. Milt and soap can be contacted for any desired amount of time with the skin, for example about 2 minutes, preferably followed by rinsing.

Milt can be applied directly to the face, where it can provide several benefits including exfoliation (such properties can typically be found for other skin areas, as well). In a preferred embodiment, milt is allowed to dry into a modified mask state, which typically takes about 5 minutes. Once formed, the milt is typically left on the face for a minimum of about 20 minutes. The milt can be gently rubbed off by the finger tips, picking up loose and dead skin cells. This process can repeated as desired, typically until the face is rubbed clean. The face is then typically rinsed thoroughly with cool water and then patted dry.

Intra-lamellar gel may be applied in combination with the milt. In a preferred embodiment, the milt is applied on the face except in the immediate eye area and allowed to partially dry. The intra-lamellar gel is then applied thickly with even strokes everywhere including the immediate eye area up to the lashes, then allowed to dry. The user may feel a slight tingling and even stinging sensation after 20 minutes. The combined mask may be left on for longer periods of time if desired.

Compositions comprising intra-lamellar gel and milt may contain gel:milt in either a 1:1 (volume:volume) or a 2:1 ratio (volume:volume). Such compositions may also contain emollients, such as vitamin A. Typically, intra-lamellar gel-milt compositions are used for skin treatment.

Intra-lamellar gel with milt when applied to the face or other skin accelerates exfoliation and absorption. There may be additional benefits with protein absorption. There may also be some balancing activity between acid and alkaline properties from each of the milt and the intra-lamellar gel, which may be better for long term use in interacting with the skin's pH balance and protein absorption.

Preferably, the milt is used first, rinsed, then the intra-lamellar gel is applied, usually in the form of a 20 minute mask. The intra-lamellar gel appears to carry the milt further into the skin because it causes at stinging sensation for the first about 2–5 minutes. Results may include smoother skin with certain skin types than using the intra-lamellar gel alone. Optionally, intra-lamellar gel may comprise a neroli essential oil.

For hair, it is preferred to use milt first (with shampoo) followed by administering the intra-lamellar gel to the wet hair. This can produce body and hold without stickiness or drying.

Examples of actual use of intra-lamellar gel and milt have been included in the discussion above. The following Examples are offered as further illustration, and not by way of limitation.

EXAMPLES

Example 1

Harvesting of Algae

The plants were harvested from marine sources. The interior cell walls of the plants had thickened, perhaps with the auxiliary cells. Algae were examined by sight. Blades were cut at the base, above the holdfast, and can be harvested on the beach (where the blades have already broken away) so as not to disturb the growth cycles. Approximately 10 lbs of material at this stage can produce approximately 1–1.2 quarts of intra-lamellar gel when brewed in water with eucalyptus oil and varying amounts with other oils.

The blades were stored at varying temperatures between 40° F. and 65° F. It was preferable to keep them at between 52° F. and 56° F.

Example 2

Brewing of Algae

The blades were examined and lightly rinsed in tap water. Non-suitable blades were discarded or utilized for fertilizer. Suitable blades were placed in 80° F.–95° F. tap water in stainless steel containers along with an essential oil for a brewing cycle from 8 hours to 15–18 hours. The essential oil was placed first in the containers, and stirred to allow for dispersal prior to inserting algae. Typically, 3 to 5 pounds of algae were combined with 5 to 10 quarts of water, and 1 to 5, preferably, 2.5 to 3, tablespoons of oil.

Two cycles of heating and cooling were used during which a minimal amount of alternating low heat was applied. The temperature of the water was raised to an optimal level of about 115° F.–118° F., preferably not to exceed 125° F.–49° C. The heating element was immediately shut down at about 115° F.–118° F., and cooled for up to 12 hours, preferably about 5–8 hours. After the cooling period, the cycle was repeated one more time until the product was ready for the next phase.

A third heating and cooling cycle was added to experiment with additional oils, such as lemon oil, to see if there was an increased amount of extractable material. Another heating cycle did not render additional material but the lemon oil was found to enhance the production of intra-lamellar gel from within the same algae blades that produced little material with eucalyptus oil.

The blades were gently removed and placed in a colander or on paper towels or gently hung at a sloped angle to help coagulate product. The water was allowed to drain from the blades. The blades were left in this position up to 8 hours. Typically, the blades were kept at about 55° F.–68° F. during this period.

Example 3

Extraction Of The Intra-Lamellar Gel

The blades were held to the light and then individually "milked" (hand expressed) into glass containers and then strained once or twice for clarifying purposes. The resulting intra-lamellar gel was placed in glass bottles with rubberized tops. The gel can also be packaged in specialty bottles such as eyedropper style bottles, which may enhance shelf life. Any bottles that come into contact with the gel should first be sterilized, for example, using alcohol. Preferably, bottles that contain the gel are hermetically sealed.

Although the present invention had been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

What is claimed is:

1. A method of producing an intra-lamellar gel from marine algae, comprising:
    (a) heating a mixture comprising blades of said algae at least one essential oil, and water to a first temperature of about 115°–35° F.;
    (b) cooling the mixture to a second temperature below about 105° for a time sufficient to form an intra-lamellar gel in said algae blades; and
    (c) isolating said intra-lamellar gel from said algae blades.

2. The method of claim 1 wherein said mixture contains more than one essential oil.

3. The method of claim 1 wherein the first temperature is about 115°–125° F., the second temperature is about 55°–105° F., and the time is about 2–48 hours.

4. The method of claim 1 wherein the first temperature is about 115°–118° F., the second temperature is about 70°–105° F., and the time is about 4–22 hours.

5. The method of claim 1 wherein the heating and cooling steps form a brewing cycle, and the brewing cycle is repeated at least once before isolating the intra-lamellar gel.

6. The method of claim 1 wherein the step of removing includes milking the intra-lamellar gel from between the blades of the algae.

7. An intra-lamellar gel obtained from blades of marine algae by the process according to claim 1.

8. A cosmetic composition comprising an intra-lamellar gel according to claim 1.

* * * * *